US005219836A

United States Patent [19]

Watkins et al.

[11] Patent Number: 5,219,836

[45] Date of Patent: Jun. 15, 1993

[54] USE OF TETRAHYDRO-4-METHYL-2-PHENYL-2H-PYRAN AS PERFUMING INGREDIENT

[75] Inventors: Hugh Watkins, Lincroft; Olamay C. Liu, Princeton, both of N.J.; James A. Krivda, Bristol, Pa.

[73] Assignee: Firmenich SA, Geneva, Switzerland

[21] Appl. No.: 920,239

[22] Filed: Jul. 27, 1992

[51] Int. Cl.[5] .................................................. A61K 7/46

[52] U.S. Cl. ........................................ 512/11; 549/356; 252/174.11; 252/8.6; 424/76.4; 424/65

[58] Field of Search .......................... 512/11; 549/356; 252/174.11, 8.6; 424/76.4, 65

[56] References Cited

U.S. PATENT DOCUMENTS

| | | | |
|---|---|---|---|
| 4,115,406 | 9/1978 | Vinals et al. | 549/356 |
| 4,914,083 | 4/1990 | Wiegers et al. | 512/11 |

FOREIGN PATENT DOCUMENTS

| | | | |
|---|---|---|---|
| 655932 | 5/1986 | Switzerland | 549/356 |
| 502892 | 2/1976 | U.S.S.R. | 549/356 |

*Primary Examiner*—James H. Reamer

*Attorney, Agent, or Firm*—Pennie & Edmonds

[57] ABSTRACT

Tetrahydro-4-methyl-2-phenyl-2H-pyran is useful as a perfuming ingredient for the preparation of perfuming compositions and perfumed articles, to which it imparts odor notes of the green, rose oxide type.

6 Claims, No Drawings

USE OF TETRAHYDRO-4-METHYL-2-PHENYL-2H-PYRAN AS PERFUMING INGREDIENT

BRIEF SUMMARY OF THE INVENTION

The present invention relates to a method to confer, enhance, improve or modify the odor properties of a perfuming composition or a perfumed article, which method comprises adding to said composition or article a fragrance effective amount of tetrahydro-4-methyl-2-phenyl-2H-pyran.

The invention relates also to a perfuming composition or a perfumed article containing as a perfuming ingredient tetrahydro-4-methyl-2-phenyl-2H-pyran.

A further object of the invention is a compound selected from the group a) and b) wherein a) is cis-tetrahydro-4-methyl-2-phenyl-2H-pyran and b) is trans-tetrahydro-4-methyl-2-phenyl-2H-pyran.

BACKGROUND OF THE INVENTION

The invention relates to the field of perfumery and in particular to the use of a substituted tetrahydro-pyran as a perfuming ingredient.

It is known from Swiss patent no. 655 932 that the hydro-pyrans of formula (I)

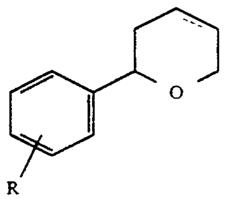

having an additional double bond in one of the positions indicated by the dotted lines and wherein R represents hydrogen or a lower alkyl radical, are useful starting materials for the synthesis of odorant molecules. There is no mention, however, nor even suggestion, in this document that the said compounds (I) might have any other potential usefulness, namely for the perfume industry.

On the other hand, the compound of formula (II)

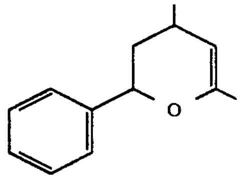

is a known fragrance ingredient, commercialized under the tradenames of PELARGENE ® (origin: PPF Int., UK) and FENYRANE ® (origin: Naarden Int., Holland). The odor of compound (II) has been described as being of the rose-geranium, rose oxide type. We have found that PELARGENE ® possesses a bitter, earthy, metallic note with some geranium character.

In a recent publication appearing in J. Org. Chem. 56, 5245 (1991), dealing with the cyclization of alkoxymethyl radicals, V. H. Rawal et al. have reported the preparation of a cyclization product which contained tetrahydro-4-methyl-2-phenyl-2H-pyran as a minor component. The latter does not appear to have been separated from the mixture obtained in the cyclization reaction and the article is totally mute as to the properties of the obtained products.

It is therefore quite unexpectedly that we have now discovered that tetrahydro-4-methyl-2-phenyl-2H-pyran possesses very useful odor properties.

THE INVENTION

It is an object of the present invention to provide a method of use of tetrahydro-4-methyl-2-phenyl-2H-pyran in perfumery as described above. This compound is in fact capable of imparting a very fresh and green odor note, with a rosy character, to the compositions and articles into which it is incorporated.

In addition, it has also been established that, despite the similarity of their structures, the present compound and prior known compound (II) are quite distinct olfactively. The latter compound has been found to possess a bitter earthy note, with some floral character and the comparative examples presented further on clearly show the difference in olfactive effects that can be obtained with the two compounds above-cited.

We have also observed that tetrahydro-4-methyl-2-phenyl-2H-pyran can be useful in many types of perfuming compositions, to which it confers original and advantageous effects. For example, it has been found to freshen the top note of aromatic-herbaceous-cologne type base compositions and to increase the body of fruity type fragrances, to which it adds a surprisingly novel twist. This compound also helps to blend the dry-down of woody, ionone and mossy type fragrances, imparting a richer effect.

Moreover, although the present compound develops an odor possessing a rosy character reminiscent of that of rose oxide, its olfactive performance is quite distinct from that of the latter. When evaluated at the same concentration in a woody type composition, containing cedarwood essential oil, synthetic sandalwood oil, synthetic patchouli oil, synthetic vetyver oil, methyl ionone and tert-butyl-cyclohexyl acetate (high content of cis-isomer), rose oxide imparted a sweet vetyver character when added to the base composition while tetrahydro-4-methyl-2-phenyl-2H-pyran gave a distinct patchouli type character to the same composition.

Owing to its structure, tetrahydro-4-methyl-2-phenyl-2H-pyran can possess two isomeric forms of formula

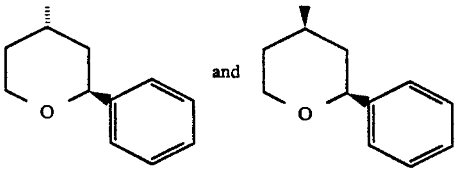

trans-isomer cis-isomer

These two isomers, of novel structure, are also the object of the present invention. They develop quite distinct odors, the cis-isomer having a green, rose oxide-diphenyloxide type note, very powerful, while the trans isomer has a much weaker odor with a green, vegetable, slightly dirty and minty character and a floral undertone. Both of these compounds can be useful in perfumery, but the cis-isomer is preferred for the applications according to the present invention. In the description and examples presented hereinafter, whenever reference is made to the use of tetrahydro-4-methyl-2-phenyl-2H-pyran, it is meant to refer to the use of any mixture of the two isomers, in particular the mixtures rich in cis-isomer, as well as to the use of said cis-isomer in its pure form.

Due to its olfactive properties, tetrahydro-4-methyl-2-phenyl-2H-pyran is useful in the preparation of perfumes and concentrated perfuming bases as well as for perfuming a variety of articles such as soaps, bath or shower gels, shampoos and other hair-care products, cosmetic preparations, air and body deodorants, detergents, fabric softeners, and household products.

As it is often the case in perfumery, the compound can be used as a perfuming ingredient either alone or in admixture with other perfuming coingredients, solvents or adjuvants of current use.

The concentrations in which the compound of the invention can be used for the above-mentioned applications vary in a wide range of values, which are a function, amongst other parameters, of the nature of the product to be perfumed and of the desired perfuming effect. By way of example, concentrations of the order of 0.1–0.5 to 10% by weight, or even more, can be cited when the compound is used in perfuming bases and concentrates. Considerably lower concentration values than those cited can be employed when the compound is used for perfuming the variety of functional articles mentioned above.

Tetrahydro-4-methyl-2-phenyl-2H-pyran as an isomeric mixture or in its cis and trans form were prepared as described hereinafter.

In an autoclave, 10 g of a mixture of 5,6-dihydro-4-methyl-2-phenyl-2H-pyran and tetrahydro-4-methylene-2-phenyl-2H-pyran (prepared from benzaldehyde and isoprenol as described in Swiss Pat. No. 655 932) in 50 ml of ethyl alcohol were hydrogenated in the presence of 0.1 g of 10% Pd on charcoal to yield 9.7 g of pure tetrahydro-4-methyl-2-phenyl-2H-pyran.

In order to separate the two isomers of the compound obtained as described above, the latter was injected in a polar column of the Megabore 30 m DB WAX type. The cis isomer had a retention time of 27.685 min, while the trans isomer presented a retention time of 28.475 min. The olfactive evaluation of these two peaks provided the result already described above and was further confirmed by gaz chromatographic separation of the pure isomers which presented the following analytical data:

cis-isomer

NMR(13C) (90 MHz, CDCl3): 22.2(q, CH3); 30.8(d, C(4)); 34.5(t, C(5)); 42.8(t, C(3)); 68.5(t, C(6)); 79.8(t, C(2)); 125.8(d, C(2')); 127.2(d, C(4')); 128.3(d, C(3')); 143.3(s, C(1'))d ppm NMR(1H) (360 MHz, CDCl3): 0.99(d, J=7, 3H); 1.24(m, 1H); 1.34(m, 1H); 1.62(m, 1H); 1.78(m, 1H); 1.85(m, 1H); 3.60(m, 1H); 4.15(ddd, J=12,4,5,2, 1H); 4.31(dd, J=11, 2, 1H); 7.22–7.37(br m, 5H)d ppm SM: 176(M+, 100), 175(88), 105(57), 77(22), 55(20), 107(19), 42(17), 41(16), 91(15), 69(14), 39(14), 106(13).

trans-isomer

NMR (13C): 18.5(q, CH3); 25.3(d, C(4)); 32.1(t, C(5)); 39.0(t, C(3)); 63.0(t, C(6)); 74.0(d, C(2)); 126.1(d, C(2')); 127.0(d, C(4')); 128.3(d, C(3')); 143.0(s, C(1'))d ppm.

NMR(1H): 1.17(d, J=7, 3H); 1.34(m, 1H); 1.80–1.99(m, 3H); 2.10(m, 1H); 3.80–3.85(m, 2H); 4.67(dd, J=10, 3, 1H); 7.22–7.37(br. m, 5H)d ppm SM: practically identical to cis-isomer.

The invention will now be described in greater detail by way of the examples presented hereinafter.

EXAMPLE 1

Perfuming composition

A base perfuming composition was prepared by admixture of the following ingredients:

| Ingredients | Parts by weight |
|---|---|
| Allyl amyl glycolate | 25 |
| 10% Ambrox ® 1) DL | 20 |
| Bergamot oil | 150 |
| Brazil Rosewood oil | 35 |
| Citral | 10 |
| 10% α-Damascone | 20 |
| Dihydromyrcenol 2) | 260 |
| Hydroxycitronellal | 15 |
| ISO E Super 3) | 40 |
| Juniper oil | 20 |
| Lavandin oil | 50 |
| Lynalyl acetate | 70 |
| 10%* Cryst. methylnaphthylketone | 35 |
| Crystal moss | 5 |
| Hedione ® 4) | 85 |
| Brazil peppermint oil | 5 |
| Vertofix coeur 5) | 125 |
| 10%* Zestover 6) | 25 |
| TOTAL | 995 |

*in dipropylene glycol
1) tetramethyl perhydronaphthofuran origin: Firmenich SA, Geneva, Switzerland
2) 2,6-dimethyl-7-octen-2-ol; origin: International Flavors and Fragrances Inc., USA
3) 2-acetyl-1,2,3,4,6,7,8-octahydro-2,3,8,8-tetramethyl naphthalene; origin: International Flavors & Fragrances Inc., USA
4) methyldihydrojasmonate; origin: Firmenich SA, Geneva, Switzerland
5) origin: International Flavors and Fragrances Inc., USA
6) 2,4-dimethyl-3-cyclohexene-1-carbaldehyde; origin: Firmenich SA, Geneva, Switzerland To this base composition there were added 5 parts by weight of tetrahydro-4-methyl-2-phenyl-2H-pyran. A novel composition was thus obtained, wherein the top note was perfectly blended to the body of the base, while the latter had become richer and more complex.

EXAMPLE 2

Perfuming composition

A base perfuming composition was prepared by admixture of the following ingredients:

| Ingredients | Parts by weight |
|---|---|
| Ambrox ® 1) DL | 15 |
| Bergamot oil | 90 |
| 10%* Calone 12) | 8 |
| 10%* α-Damascone | 15 |
| Dihydromyrcenol 2) | 75 |
| Exolide ® 3) | 100 |
| Florol ® 4) | 15 |
| 10%* Galbanum oil | 15 |
| Galbex ® 5) | 40 |
| China geranium oil | 10 |
| Geranyl acetate | 5 |
| 10%* Heliopropanal | 8 |
| Hydroxycitronellal | 10 |
| ISO E Super 6) | 25 |
| Juniper essential oil | 12 |
| 50%* Labdanum resinoid | 10 |
| Lavandin oil | 30 |
| Linalol | 30 |
| Linalyl acetate | 50 |
| 1%* Melonal ® 7) | 25 |

-continued

| Ingredients | Parts by weight |
|---|---|
| 10%* Methyl anthranilate | 5 |
| 10%* Cryst. methylnaphthylketone | 25 |
| 10%* Methyl nonyl acetaldehyde | 3 |
| Crystal moss | 5 |
| Hedione ® 8) | 55 |
| Florida orange oil | 20 |
| Polysantol ® 9) | 20 |
| Clary sage oil | 8 |
| Spearmint oil | 4 |
| Vertofix coeur 10) | 80 |
| Haiti vetyver oil | 12 |
| 10% Zestover ® 11) | 15 |
| TOTAL | 840 |

*in dipropylene glycol
1) see example 1
2) see example 1
3) cyclopentadecanolide; origin: Firmenich SA, Geneva, Switzerland
4) tetrahydro-2-isobutyl-4-methyl-4(2H)-pyranol; origin: Firmenich SA, Geneva, Switzerland
5) origin: Firmenich SA, Geneva, Switzerland
6) see example 1
7) 2,6-dimethyl-5-heptenal; origin: Givaudan-Roure, Vernier, Switzerland
8) methyldihydrojasmonate; origin: Firmenich SA, Geneva, Switzerland
9) 3,3-dimethyl-5-(2',2',3'-trimethyl-3'-cylopent-1'-yl)-4-penten-2-ol origin: Firmenich SA, Geneva, Switzerland
10) see example 1
11) see example 1
12) 2,4-dihydro-8-methyl-1,5-benzo[b]dioxepin-3-one; origin: CAL Pfizer When 160 parts by weight of tetrahydro-4-methyl-2-phenyl-2H-pyran were added to this base composition, a novel composition was obtained which developed a much stronger odor, with a reinforced green, rosy-floral character.

When an identical amount of Pelargene ® was added to the base composition, the latter developed a metallic, geranium note with less diffusion and strength.

What we claim is:

1. A method to confer, enhance, improve or modify the odor properties of a perfuming composition or a perfumed article, which method comprises adding to said composition or article a fragrance effective amount of tetrahydro-4-methyl-2-phenyl-2H-pyran.

2. A method according to claim 1, wherein tetrahydro-4-methyl-2-phenyl-2H-pyran is added in the form of its cis-isomer.

3. A perfuming composition or a perfumed article containing as a perfuming ingredient tetrahydro-4-methyl-2-phenyl-2H-pyran.

4. A perfuming composition or a perfumed article according to claim 3, wherein tetrahydro-4-methyl-2-phenyl-2H-pyran is in the form of its cis-isomer.

5. A perfumed article according to claim 3, in the form of a perfume or a cologne, a soap, a shower or bath gel, a shampoo or other hair-care product, a cosmetic preparation, an air or body deodorant, a detergent or a fabric softener, or a household product.

6. A compound selected from the group a) and b), wherein a) is cis-tetrahydro-4-methyl-2-phenyl-2H-pyran and b) is trans-tetrahydro-4-methyl-2-phenyl-2H-pyran.

* * * * *